United States Patent [19]

Storz

[11] 4,276,878
[45] Jul. 7, 1981

[54] INJECTION SYRINGE

[76] Inventor: Karl Storz, Auf dem Schildrain 39, 7200 Tuttlingen, Fed. Rep. of Germany

[21] Appl. No.: 67,812

[22] Filed: Aug. 20, 1979

[51] Int. Cl.$^3$ ............................................. A61M 5/00
[52] U.S. Cl. .............................. 128/218 PA; 128/234
[58] Field of Search ................ 128/261, 218 C, 218 P, 128/218 PA, 234, 236, 217, 215, 213; 222/326, 386.5

[56] References Cited

U.S. PATENT DOCUMENTS

| | | | |
|---|---|---|---|
| 2,883,984 | 4/1959 | Candido, Jr. et al. | 128/217 |
| 3,110,310 | 11/1963 | Cislak | 128/218 C |
| 3,517,668 | 6/1970 | Brickson | 128/218 C |

Primary Examiner—John D. Yasko
Attorney, Agent, or Firm—Donald D. Mon

[57] ABSTRACT

An injection syringe useful in the medical arts for injecting high viscosity pastes, especially in endoscopic applications. The syringe includes a long cylinder with a relatively small diameter bore. A relatively short cannula can be connected to the cylinder to receive paste from the bore. The cylinder has a large hoop strength, and may be flexible. Paste is extruded by a piston assembly which includes a driven piston and a flexible piston rod adapted to be advanced by a grip mechanism. Preferably the piston rod is a flexible wire which includes a plurality of balls that are spindled on it, and are side-supported by the cylinder.

14 Claims, 2 Drawing Figures

INJECTION SYRINGE

FIELD OF THE INVENTION

This invention relates to the injection of high viscosity pastes, and more particularly to an injection syringe useful for injecting such pastes in surgical procedures, especially in endoscopic procedures.

BACKGROUND OF THE INVENTION

The present invention relates to an injection syringe, particularly for medical purposes, for injecting high viscosity pastes and whose actuating parts constructed in the form of gripping handles with notches engage in a piston rod provided with corresponding step-like parts and which can be advanced stepwise into the syringe cylinder together with the syringe piston.

The known injection syringes of this type are constructed inter alia with a long injection cannula, which is slightly elastic and can be introduced into a corresponding channel of an endoscope. The syringe cylinder must remain outside the endoscope, because not only is it rigid, but also has a larger diameter than the endoscope channel, e.g. 12 mm.

In the field of medicine, generally liquids are injected. The higher the viscosity of the liquids to be injected the higher must be the pressure in order to force the liquid through the thin injection cannula. For injecting highly viscous substances, e.g. pastes, syringes of the type indicated hereinbefore are known, whose piston rod is constructed in the manner of a rack. By a corresponding transmission ratio of the actuating parts the rack can be advanced in stepwise manner with a much larger force than in conventional syringes. However, the diameter is so large that, despite the relatively high force, the paste generally remains stuck in the long cannula.

BRIEF SUMMARY OF THE INVENTION

The problem of the invention is to obviate these disadvantages and to so improve the injection syringe of the type indicated hereinbefore that it is easily possible to apply a much higher pressure to the paste whilst exerting the same or a reduced force, so that the paste is advanced with maximum reliability and never gets stuck in the cannula.

The invention is based on the finding that for a given applied force the pressure per unit area on the paste increases in inverse proportion to the effective piston surface and the corresponding internal diameter of the cylinder. As is known the force applied to the piston is distributed in such a way that the pressure is calculated from this force per effective piston area.

According to the invention this problem is solved in that the piston rod and cylinder are made thin and long and are made at least partly flexible.

The term "thin" in the present context means that the cylinder has a thickness of less than 10 mm and preferably very few mm. In order to be able to still inject the necessary quantity without it being necessary to recharge the syringe according to the invention the piston rod and cylinder are made slightly elastic, so that they can be introduced like a cannula into an endoscope.

According to a further development of the invention, the piston rod has juxtaposed members which are at least partly elastic relative to one another.

This means that the members can at least move slightly relative to one another, so that the necessary flexibility of the piston rod according to the invention is ensured.

According to a further feature of the invention, the piston rod has a relatively thin core wire on which are juxtaposed in a row, balls drilled with a larger diameter than the core wire, but a smaller diameter than the internal diameter of the cylinder, being axially positioned between a stop member on the piston rod end and the piston.

As a result of the balls the wire, which can be extremely thin, is prevented from being laterally deflected and can even be precisely guided by the balls in the cylinder which can be constructed as a plastic hose. The notch on the actuating lever then engages between two of these balls and presses all the loosely juxtaposed balls forward and against the plunger.

It is also advantageous for the length of the cylinder to be a multiple of its diameter.

In fact the length of the syringe cylinder and the piston are not limited. Provided that the piston rod is located outside the gripping handle the operator is not impeded, because as a result of the invention the piston rod is not rigid but slightly elastic. For example the syringe cylinder length can be 10 to 100 times the diameter.

BRIEF DESCRIPTION OF THE DRAWINGS

The invention is described in greater detail hereinafter relative to a non-limitative embodiment and with reference to the drawings, in which.

DETAILED DESCRIPTION OF THE PREFERRED EMBODIMENTS

Figure 1:
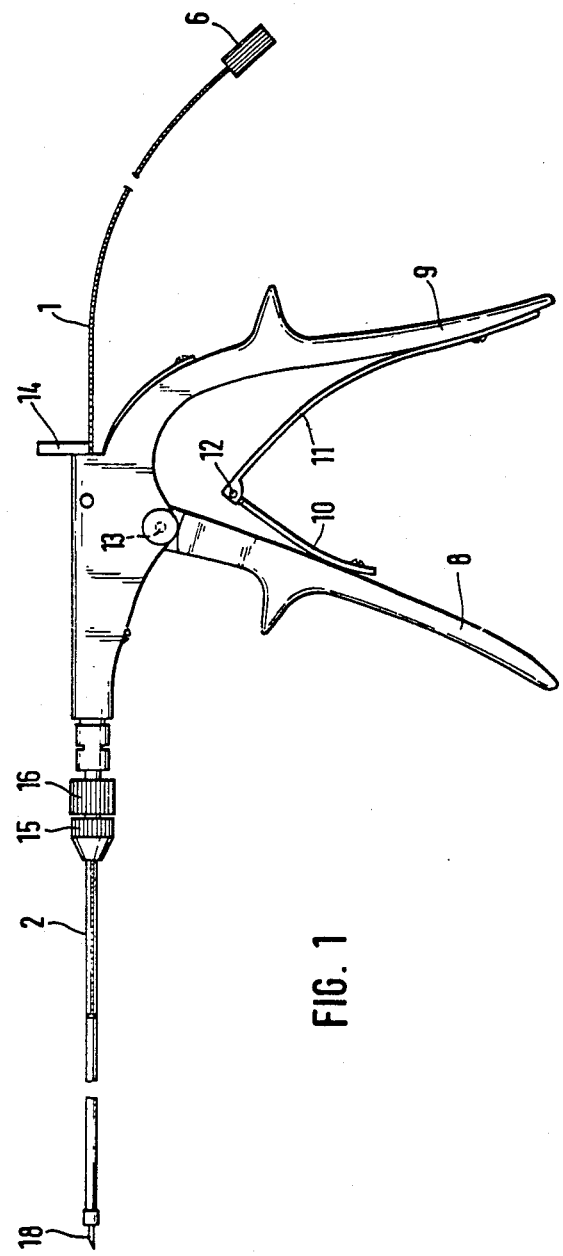
FIG. 1 is a side view of the object of the invention.

FIG. 1 shows the two gripping handles 8 and 9, between which are arranged the two spring members 10 and 11, interconnected in articulated manner about the pivot 12, whilst the two gripping handles are relatively pivotable about point 13 that portion of handle 9 above point 13 is sometimes referred to as a "frame". The details of this gripping handle system are well known to the Expert, and are conventionally used for advancing rigid racks. To the right in the drawing can be seen the piston rod 1 with its reinforcing collar 6 on the end, as will be described in greater detail hereinafter. The piston rod is introduced into a channel in the gripping handle 9 to the left, which issues into the cylinder 2, to whose end is fixed the injection cannula 18. To gripping handle 9 is fixed a pawl 14 which, when pivoted upwards, prevents piston rod 1 from sliding back to the right. "Piston advancing means" is provided as an extension of the pivoted handle system, for the purpose of engaging and abutting step-like parts (discontinuities) on the piston so as to advance the piston to the left in FIG. 1 when handles 8 and 9 are squeezed toward one another. The piston advancing means can constitute structure such as notches which can make driving engagement with discontinuities on the piston (i.e., with the balls). The handles 8 and 9 are sometimes collectively referred to as "grip means". Further to the left is provided, inter alia, a conical locking screw 15 which is intended to screw cylinder 2, which is made from an elastic (flexible) plastic material, to the metal part.

The cylinder 2 can have a considerable length 1 of e.g. 1 m, whilst in general its diameter d is only a few mm.

Figure 2:
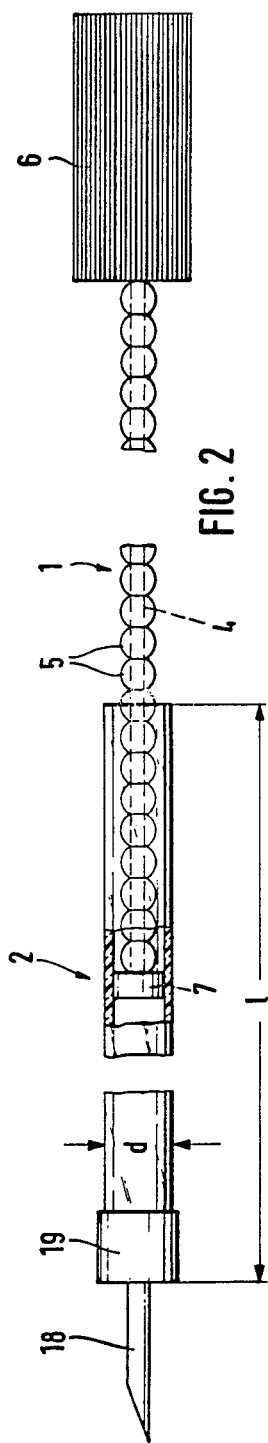
FIG. 2 is a side view of the cylinder, greatly enlarged for purposes of illustration, with its piston and piston rod.

FIG. 2 shows cylinder 2 and piston 1 according to the invention in greatly enlarged form. It is once again possible to see at the left-hand end the relatively short cannula 18 with a reinforcing collar 19, which can be constructed as a cap for cylinder 2. This injection cannula can be sealed in, its length needing only to be a few mm. Further to the right can be seen the piston 7 fitted into cylinder 2, whereby said piston can be connected with a relatively thin and partly elastic (flexible) wire 4 as the actuating member, which is surrounded by balls 5 which are juxtaposed in a row. The balls are drilled with a diameter corresponding to wire 4 and have an external diameter corresponding to the internal diameter of cylinder 2. As a result the relatively thin wire 4 is elastically guided in cylinder 2, so that it can transmit a relatively larger force the balls are a "step-wise" part of the piston, and they constitute discontinuities along its length which can be engaged and moved by the piston advancing means.

Further to the right it is possible to see the piston rod 1 alone, and at its end is provided endpiece 6 connected to the core wire 4.

Syringe cylinder 2 preferably comprises a plastic material such as Teflon. This plastic material has the advantage that it not only has the necessary elasticity (flexibility), but also the corresponding strength, because a very high pressure is formed in cylinder 2 by a given force in view of the very small diameter d. The force exerted by the hand is transmitted from gripping handle 8 via pivot 13 of a lever to a not shown relatively short lever, so that there is a very considerable increase in force which presses piston rod 1 according to FIG. 1 from right to left into cylinder 2.

For charging the syringe the pawl 14 is shifted and piston rod 1 is drawn back manually to the right until it is out of cylinder 2. The sleeve nut 16 is then loosened-it can be the actuation for a metal bayonet catch. The paste is now introduced into this end in the vicinity of nut 16 and is fed manually with piston 7 and piston rod 1. The paste tubes are actually constructed in such a way that they themselves provide the pressure necessary for advancing the paste in cylinder 2, so that feeding with piston 7 can also be eliminated.

After syringe cylinder 2 has been filled in this way, the piston is introduced into endpiece 16 which is then screwed down. Pawl 14 is then pivoted upwards again and the syringe is ready to operate. As stated hereinbefore it is generally used in a medical endoscope. To this end cylinder 2 is introduced into the not shown instrument channel of a medical endoscope, as is obvious to the Expert without its being represented in the drawings.

By actuating the gripping handle 8 relative to gripping handle 9, piston 7 can easily be advanced into cylinder 2 to such an extent that all the paste is forced through the injection cannula 18. Due to the indicated dimensions a high pressure is exerted on the very small active area of the piston 7, which is only a few mm².

Even though piston rod 1 is still outside gripping handle 9, the operator is not impeded despite the piston rod length, because the latter is elastic (flexible) and hangs downwards in the indicated manner.

The invention is not limited to the represented embodiment. For example balls 5 can be replaced by differently shaped segments, e.g. short cylinders, which are spherical at the front and rear. According to the invention it is decisive that piston rod 1 comprises link-like elastic (flexible) parts which match the elastic cylinder.

What is claimed is:

1. An injection syringe for injection of high viscosity pastes comprising: a frame; a pair of handles mounted to said frame, at least one of which is pivotally mounted to said frame, said handles comprising grip means which can be squeezed to move the handles toward one another; an elongated cylinder mounted to and projecting beyond said frame having a first end spaced from said frame to which an injection cannula can be mounted; a piston slidably fitted in said cylinder; a piston rod connected to said piston and extending from the other end of said cylinder, said piston having discontinuities along its length; piston advancing means connected to said grip means and adapted to engage said discontinuities to move said piston rod and piston toward said end when said grip means is squeezed, at least that portion of said cylinder which is adjacent to its first end being flexible, and at least that portion of said piston rod which occupies said portion of said cylinder when said piston is adjacent to said first end being flexible, the ratio of the length diameter and wall thickness of said portion of said cylinder being such that said cylinder with the rod inside it can be bent and still allow the advance of the piston rod and piston to eject paste from said cylinder through said cannula.

2. An injection syringe according to claim 1, wherein the piston rod carries juxtaposed members which are at least partly movable relative to one another.

3. An injection syringe according to claim 1, wherein the piston rod comprises a relatively thin core wire on which are juxtaposed in a row balls drilled with a larger diameter than the core wire, but a smaller diameter than the internal diameter of the cylinder, said balls being axially positioned between a stop member on the piston rod end and the piston.

4. An injection syringe according to claim 1, wherein the length of the cylinder is a substantial multiple of its diameter.

5. An injection syringe according to claim 4, wherein the length of the syringe cylinder is 10 to 100 times its inside diameter.

6. An injection syringe according to claim 1, wherein the syringe cylinder is made from a flexibly elastic plastics material.

7. An injection syringe according to claim 1 which further includes a said injection cannula of relatively short length mounted to said first end, said injection cannula having a reinforcement for insertion into an endoscope.

8. An injection syringe according to claim 7 in which the inside diameter of said injection cannula at its end farthest from said first end of said cylinder is smaller than the inside diameter of said cylinder.

9. An injection syringe according to claim 8 in which the diameter, wall thickness and physical properties of said cylinder enable it to be flexed with said piston rod inside it.

10. An injection syringe for high viscosity pastes comprising:
a relatively long cylinder;
a cannula connected to said cylinder to receive paste from said cylinder;
a piston in said cylinder for extruding said paste through said cannula;

an elongated flexible piston rod extending into said cylinder and connected to said piston for advancing said piston in said cylinder;

a grip assembly incorporating piston advancing means for advancing said piston rod in said cylinder;

said piston rod comprising a plurality of balls spindled on a flexible wire for engagement by said piston advancing means.

11. The injection syringe according to claim 8 wherein said cylinder is removable from said grip assembly for insertion of said paste.

12. The injection syringe according to claim 10 wherein the diameters of said plurality of balls on said piston rod are approximately equal to or slightly less than the internal diameter of said cylinder.

13. The injection syringe according to claim 10 wherein the length of said cylinder is in the range of 10 to 100 times the diameter.

14. The injection syringe according to claim 11 including a pawl on said handle assembly for releasing said piston assembly for retraction from the cylinder when filling with a high viscosity paste.

* * * * *